United States Patent
Pinnell

(10) Patent No.: US 6,524,599 B2
(45) Date of Patent: Feb. 25, 2003

(54) USE OF MILK THISTLE EXTRACT IN SKIN CARE COMPOSITIONS

(75) Inventor: Sheldon R. Pinnell, Durham, NC (US)

(73) Assignee: Skinceuticals, Inc., Garland, TX (US)

( * ) Notice: Subject to any disclaimer, the term of this patent is extended or adjusted under 35 U.S.C. 154(b) by 34 days.

(21) Appl. No.: 09/895,970

(22) Filed: Jun. 29, 2001

(65) Prior Publication Data

US 2002/0155074 A1 Oct. 24, 2002

Related U.S. Application Data

(60) Provisional application No. 60/270,505, filed on Feb. 21, 2001.

(51) Int. Cl.⁷ .............................. A61K 6/00; A61K 7/00; A61K 7/04; A61K 7/06
(52) U.S. Cl. ........................ 424/401; 424/70.1; 424/61
(58) Field of Search .................. 424/401, 61, 70.1

(56) References Cited

U.S. PATENT DOCUMENTS

| | | | |
|---|---|---|---|
| 4,895,839 A | 1/1990 | Bombardelli | 514/78 |
| 4,997,649 A | 3/1991 | Papaconstantin et al. | 424/195 |
| 5,804,168 A | 9/1998 | Murad | 424/59 |
| 6,147,054 A | 11/2000 | De Paoli Ambrosi | 514/23 |

Primary Examiner—Thurman K. Page
Assistant Examiner—S. Howard
(74) Attorney, Agent, or Firm—Jenkens & Gilchrist, P. C.

(57) ABSTRACT

The present invention relates to the use of compositions comprising the extract of the milk thistle plant, *Silybum marianum*, soybean protein and alpha tocopherol, either singly or in combination, in novel compositions for topical application on skin, hair and nails. More specifically, the present invention pertains to compositions for the above use, which are suitable for the entire skin. The present invention pertains to compositions for the above use, which are characterized in that they comprise milk thistle extract, soybean protein, and alpha tocopherol, either individually or in combination.

14 Claims, No Drawings

USE OF MILK THISTLE EXTRACT IN SKIN CARE COMPOSITIONS

CROSS-REFERENCES TO RELATED APPLICATIONS

This Application for Patent claims the benefit of priority from, and hereby incorporates by reference the entire disclosure of, co-pending U.S. Provisional Application for Patent Serial No. 60/270,505 filed Feb. 21, 2001.

TECHNICAL FIELD OF THE INVENTION

The present invention is related to compositions comprising the extract of the milk-thistle plant (*Silybum marianum*), soybean protein, and alpha tocopherol, either singly or in combination, for application to skin, hair and nails.

BACKGROUND OF THE INVENTION

The skin is the largest organ of the human body, which primarily functions to protect the body's internal organs from the outside environment. The outside environment that the skin must endure may consist of large fluctuations in both temperature and humidity. Further, the skin may be exposed to radiation from the sun or other sources. Additionally, the skin is routinely exposed to wind, dust, dirt and other harsh chemicals. Finally, the skin must survive the daily rituals that may include washing, shaving, and/or the application of cosmetics.

These environmental factors contribute to the aging of the skin. In particular, these environmental factors have been known to cause aging lines, wrinkles, skin dryness characterized by the loss of the skin's natural oils and moisture, skin fading, age spots, and the loss of skin elasticity.

As humans age, the skin becomes dry, loses its elasticity, and begins to wrinkle. These are the primary visible effects of chronological aging. Following menopause, it has been shown that skin thickness decreases and collagen levels in the skin diminish, which may further contribute to these negative age-related changes in the skin. Scientific studies strongly suggest that these changes may be attributed to menopausal and/or age-related hormonal fluctuations. More specifically, research suggests that estrogen deficiency may primarily be responsible.

Estrogen works by interacting with estrogen receptors in the body and signaling genes in cells to be switched on or off. Flipping these switches can cause the body to generate new cells or to produce special substances. Following menopause, the production of estrogen in the female body is markedly reduced. Although the exact mechanisms are unknown, this reduction in estrogen is believed to contribute to decreases in skin thickness, dryness, and loss of elasticity. Estrogen receptors have been detected in the skin. It has been shown that systemic and topical estrogen improve skin thickness, increase collagen levels, and minimize wrinkling and dryness.

Although estrogen is important, researchers also believe that decreased estrogen levels are only part of the aging equation; free radical attacks caused by exposure of the skin to environmental elements like sunlight, smoke, and pollution also contributes to premature aging of the skin. Antioxidants can help counter these effects by neutralizing free radicals, and estrogens are strong antioxidants with even stronger activity than vitamin E and vitamin C.

The extract of the milk thistle plant, *Silybum marianum*, which belongs to the aster family (Asteraceae or Compositae), comprises silymarin as the active constituent. Silymarin consists of a mixture of three bioflavinoids (flavonolignans), silybin, silydianin, and silychristine, found in the fruit, seeds, and leaves of the milk thistle plant. Silybin is the main component of silymarin, amounting to 60–70% by weight, and is thought to have the most biological activity. Standardized commercially available extracts of milk thistle, used in the preparation of the compositions of the present invention, typically contain 70–80% by weight of silymarin. These commercial preparations are variously referred to herein as milk thistle extract, lady's thistle extract, or silybum extract.

Historically, milk thistle extract has been used to treat disorders of the spleen, liver and gall bladder. Silymarin has been shown to have utility in many liver disorders including hepatitis, alcoholic liver disease, and hepatitis. It has also been shown to be useful for the treatment of toxin-induced liver toxicity including poisoning from death cap mushroom (*Amanita phalloides*). The mechanism of action for the beneficial effects of silymarin in liver disease is unknown, although antioxidant activity is a leading theory. In the animal model of cirrhosis produced by bile duct obliteration, silymarin has an antifibrotic effect. Oral doses of 1000 mg can be administered daily to humans without toxicity, and in animals, there is no known lethal dose.

Mechanistic studies have shown silymarin to be a very strong antioxidant compound capable of scavenging both free radicals and reactive oxygen species (ROS), thus increasing the antioxidant potential of cells by ameliorating the deleterious effects of free radical reactions. Furthermore, since an increase in ornithine decarboxylase (ODC) activity in epidermis is a prerequisite for skin tumor promotion, it has been shown that silymarin possesses strong inhibitory effects against the induction of epidermal ODC and messenger RNA expression in mouse models, caused by 12-O-tetradecanoylphorbol-13-acetate (TPA). In addition, silymarin has been shown to afford substantial protection against photocarcinogenesis in a mouse model. This effect of silymarin is due to the inhibition of several different events associated with UVB-induced tumor initiations and tumor promotion, by virtue of its strong anti-oxidant activity.

Soybean protein comprises soy isoflavones, which are phytoestrogens i.e., substances that mimic the activity of estrogen. The estrogenic effect of phytoestrogens is considerably weaker than estrogens, but is appreciable, and both oral and topical application of phytoestrogens have been shown to have many beneficial effects for the skin. In addition to estrogenic activity, soy isoflavones have antioxidant properties, and like other antioxidants, help to prevent free-radical damage to DNA. Phytoestrogens have also been effective for preventing skin cancer in mice, both orally and topically.

Three key isoflavones found in soy are genistein, diadzein and glycitein. Genistein is found most abundantly in soy, and there is a strong body of research supporting the benefits that genistein provides the skin. Genistein is a strong antioxidant, and may be effective in preventing cancer. Although its exact anti-cancer mechanism is unknown, genistein has been proven to protect against sunburn in humans, and to block the formation of reactive oxygen species. This makes soy isoflavones an ideal alternative to estrogen therapies, and perfect for use on maturing skin. A commercially available source for soy isoflavones used in the preparation of the compositions of the present invention, is a mixture comprising soy bean protein, water and butylene glycol. The percentage of genistein and diadzein present in the soy isoflavones used in the compositions of the present invention is between 0.01 to 0.03% by weight and 0.07 to 0.15% by weight respectively.

Vitamin E (tocopherol) is a generic term for compounds that have a 6-chromanol ring, an isoprenoid side chain, and the biologic activity of α-tocopherol. The vitamin E group contains α-, β-, γ-, and δ-tocopherols, which vary in the extent to which the chromanol ring is methylated. D-α-tocopherol is the only naturally occurring stereoisomer and the most potent in biologic assays. Vitamin E is a great source of vitamin for many different reasons including heart protection, cancer prevention, and immunity booster. Vitamin E is the body's most important lipid-soluble antioxidant, especially in cell membranes and lipoproteins. As an antioxidant, it protects other fat-soluble vitamins from oxidative damage. It is necessary for tissue repair; it is a natural anticoagulant; and promotes wound healing. The terms vitamin E and alpha tocopherol as used herein are intended to be synonymous with one another, and refer to D-α-tocopherol.

Green tea extract has been shown to have powerful anticarcinogenic properties, and has been shown to inhibit cancers in test tube and animal studies. Green tea extract contains polyphenols (also known as catechins) which are natural antioxidants. Catechins scavenge peroxyl radicals in a liposomal and in an aqueous system. Green tea polyphenols have been shown to inhibit UVB-induced non-melanoma skin cancer. Green tea extract has stronger anti-oxidant properties than vitamin E, and in addition possesses anti-inflammatory properties. Without limiting the scope of the invention, a preferred source of green tea extract is Japanese green tea extract.

The above discussion illustrates the potential uses of milk thistle extract, soybean protein and alpha tocopherol, either singly or in combination, in a manner that takes advantage of their antioxidant and anticarcinogenic properties. It is the object of the present invention to prepare a composition comprising milk thistle extract, soybean protein, and alpha tocopherol, either singly or in combination, for application on skin, hair and nails.

The compositions of the present invention differ from compositions in the prior art which comprise extracts of the milk thistle plant, for example, U.S. Pat. Nos. 6,147,054, 4,997,649, and 5,804,168. The compositions of the present invention comprise specific ingredients that are not found in the compositions of the prior art.

SUMMARY OF THE INVENTION

The present invention relates to the use of compositions comprising the extract of the milk thistle plant, Silybum marianum, soybean protein and alpha tocopherol, in novel compositions for external use to be applied on skin, hair and nails. More specifically, the present invention pertains to compositions for the above use, which are suitable for the entire skin. The present invention pertains to compositions for the above use, which are characterized in that they comprise milk thistle extract, soybean protein, and alpha tocopherol, either individually or in combination.

DETAILED DESCRIPTION OF PREFERRED EMBODIMENTS

The compositions of the present invention are related to products that may be used in the beautification, care and maintenance of health of skin, hair and nails. The compositions of the present invention can comprise, consist essentially of, or consist of, the ingredients and components described herein. As used herein, the term "consisting essentially of" means that the composition or component may include additional ingredients, but only if the additional ingredients do not materially alter the basic and novel characteristics of the claimed compositions or methods. The term "topical application", as used herein, refers to the application and/or spreading of the compositions of the present invention onto the surface of the skin, hair and nails.

The present invention relates to the use of compositions comprising milk thistle extract, soybean protein, and alpha tocopherol, either singly or in combination, for application to skin, nails and hair. In one aspect of the invention, the compositions of the present invention relate to compositions for the above uses, comprising milk thistle extract. Without limiting its scope, the composition of the present invention may be used to combat photo-aging, photo-carcinogenesis, and radiation dermatitis, and in addition, may also be used for skin lightening. The medical literature is replete with references to the utility of anti-oxidants as photoprotectants. The demonstrated lack of toxicity of milk thistle extract in combination with its antioxidant properties make it an ideal ingredient for use in skin care products for the purposes of photo-protection, and for the purposes of combating aging and carcinogenesis (photo-carcinogenesis as well as non-photo-carcinogenesis) of the skin, dermatitis, and skin inflammation conditions.

In another aspect of the invention, the compositions of the present invention comprise milk thistle extract, soybean protein, and alpha tocopherol, either singly or in combination, in a manner which takes advantage of their antioxidant and anticarcinogenic properties (discussed in greater detail in the Background section). The compositions of the present invention include compositions which comprise 1) milk thistle extract and soy bean protein, but not alpha tocopherol; 2) soy bean protein and alpha tocopherol, but not milk thistle extract; 3) milk thistle extract and alpha tocopherol, but not soy bean protein; and 4) milk thistle extract, soybean protein, and alpha tocopherol.

In yet another aspect of the invention, the compositions of the present invention comprise one or more of the following ingredients and/or components (compound name provided per CTFA "The Cosmetic, Toiletry, and Fragrance Association" guidelines, followed by trade mark, if any, under which said compound is marketed), selected from the group consisting of stearic acid; cetyl alcohol marketed under the trade mark "LIPOCOL C"; methylpolysiloxane marketed under the trade mark "SILICONE HL-88"; alpha bisabolol; hydrogenated vegetable oil marketed under the trade mark "BOIS OIL"; myristyl myristate marketed under the trade mark "LIPONATE MM"; cetyl palmitate marketed under the trade mark "CUTINA CP"; a mixture of caprylic, capric and stearic triglycerides marketed under the trade mark "SOFTSAN 378"; Petrolatum marketed under the trade mark "LLTRAPURE SC WHITE PETROLATUM"; Lauroyl Lysine marketed under the trade mark "AMIHOPE LL"; Hydrogenated Lecithin marketed under the trade mark "LECINOL S-10"; water, trisodium EDTA (trisodium ethylenediamine tetra-acetic acid); triethanolamine marketed under the trade mark "TEA 99%"; Glycerin marketed under the trade mark "GLYCERIN 99%"; aloe vera extract marketed under the trade mark "EXTRACT OF ALOE VERA 10 FOLD"; Carbomer marketed under the trade mark "CARBOPOL 940 2%"; mixture of propylene glycol; diazolidinyl urea; methylparaben and propylparaben marketed under the trade mark "GERMABEN II"; Retinyl palmitate marketed under the trade mark "VITAMIN A PALMITATE"; a mixture of butylene glycol and sea whip extract marketed under the trade mark "GORGONIAN EXTRACT"; a mixture of water, butylene glycol, and soy bean protein marketed under the trade mark "FLAVOSTER- ONE SB"; milk thistle extract marketed under the trade mark "SILYMARIN"; ethoxydiglycol marketed under the trade mark "TRIVALIN SF"; and alpha tocopherol marketed under the trade mark "VITAMIN E".

In a further aspect of the invention, the compositions of the present invention comprise one or more of the following ingredients (compound name provided per CTFA "The Cosmetic, Toiletry, and Fragrance Association" guidelines, followed by trade mark, if any, under which said compound is marketed), selected from the group consisting of water; glycerin marketed under the trade mark "GLYCERIN 99%"; ethoxydiglycol marketed under the trade mark "TRIVALIN SF"; Cyclopentasiloxane marketed under the trade mark "CYCLOMETHICONE"; Dimethicone marketed under the trade name "DIMETHICONE 200"; Dimethiconol marketed under the trade mark "CK-100"; a mixture of Cyclopentasiloxane and Dimethicone/Vinyl Dimethicone crosspolymer marketed under the trade mark "CHEMISIL SFE 938"; Dimethicone Copolyol marketed under the trade mark "ABIL B 8832"; Grape Seed Oil marketed under the trade mark "LIPOVOL G"; Sunflower seed Oil marketed under the trade mark "LIPOVOL SUN"; Sesame Oil marketed under the trade mark "LIPOVOL SES"; Soybean Oil marketed under the trade mark "LIPOVOL SOY"; Steareth 21 marketed under the trade mark "BRIJ 721"; Nylon-12 marketed under the trade mark "ORGASOL 2002 D EX NATCOS"; a mixture of Polyacrylamide, C13-14 Isoparaffin, and Laureth-7 marketed under the trade mark "SEPIGEL 305"; a mixture of Propylene Glycol, Water, and Green Tea Extract marketed under the trade mark "EXTRACT OF JAPANESE GREEN TEA"; Biosaccharide Gum-1 marketed under the trade mark "FUCOGEL 1000"; a mixture of Propylene Glycol, Water, and Cucumber Extract marketed under the trade mark "EXTRACT OF CUCUMBER"; a mixture of Phenoxyethanol, Methylparaben, Butylparaben, Ethylparaben, and Propylparaben marketed under the trade mark "PHENONIP"; Alpha tocopherol marketed under the trade mark "VITAMIN E", a mixture of water, butylene glycol, and soy bean protein marketed under the trade mark "FLAVOSTERONE SB"; a mixture of Silybum Extract (Milk Thistle Extract) and Alcohol marketed under the trade mark "PRONALEN SILYBUM HSC"; and a mixture of Ylang Ylang oil, Geranium Oil, Rose oil, Rose Absolute, and Chamomile Oil marketed under the trade mark "ALL NATURAL BLEND #32742".

The compositions of the present invention are useful for topical application i.e., on the exterior surface of the body, more preferably on, hair, skin, and nails. The compositions of the present invention are also useful for the regulation of skin condition, including the signs of skin aging described herein. As used herein, the regulation of skin condition involves improving skin appearance and/or feel. As used herein, the "regulation of skin condition" includes delaying, minimizing, preventing, and/or ameliorating the signs of skin aging. The term "signs of skin aging" as used herein include but are not limited to, all outward visible and tactile manifestations due to skin aging, including but not limited to wrinkles, skin lines, skin spots, skin discoloration, skin roughness, loss of skin firmness and/or elasticity. Such signs may be caused or induced by intrinsic or extrinsic factors, e.g., chronological aging and/or environmental damage including, but not limited to sunlight, UV radiation, smoke, ozone, and pollutants.

The compositions of the present inventions are generally prepared by conventional methods such as are known in the art of making compositions for topical application. Such methods typically involve mixing of the ingredients in one or more steps to a relatively uniform state, with or without heating, cooling, application of vacuum, and other methods.

In accordance with the present invention, the concentration of silymarin in the compositions of the present invention, is preferably in the range of 0.1 to 5.0% by weight, more preferably 0.105 to 2.1% by weight, and most preferably either one of 0.105% or 2.1% by weight. Further, the concentration of genistein and diadzein present in the soybean protein mixture used in the preparation of the compositions of the present invention are preferably in the range of 0.01 to 0.03% by weight and 0.07 to 0.15% by weight respectively. Further, the concentration of alpha-tocopherol present in the compositions of the present invention is preferably in the range of 1 to 5% by weight, more preferably 2 to 4% by weight, and most preferably 3% by weight.

The following examples further describe and demonstrate embodiments within the scope of the present invention. The examples are given solely for the purpose of illustrations, and are not intended to limit the scope of the present invention, because variations of the present invention are possible without departing from the spirit and scope of the invention.

Compositions in accordance with the present invention are shown in Working Examples 1 and 2. Unless otherwise specified, the proportions of the components comprising the compositions in Examples 1 and 2 represent the weight percentages of the respective components relative to the final product.

WORKING EXAMPLES

Example 1

In a preferred embodiment of the invention, the composition of the present invention is prepared from the following components:

| Component (CTFA Name) | % by Weight |
| --- | --- |
| Stearic Acid | 4.00 |
| Cetyl Alcohol | 1.00 |
| Methylpolysiloxane | 1.00 |
| Alpha Bisabolol | 0.50 |
| Hydrogenated Vegetable Oil | 2.00 |
| Myristyl Myristate | 4.00 |
| Cetyl Palmitate | 4.00 |
| Caprylic/Capric/Stearic Triglycerides | 0.75 |
| Petrolatum | 1.25 |
| Lauroyl Lysine | 0.50 |
| Hydrogenated Lecithin | 1.00 |
| Trisodium EDTA | 0.10 |
| Triethanolamine | 0.50 |
| Glycerin | 5.00 |
| Aloe Vera Extract | 5.00 |
| Carbomer | 20.00 |
| Propylene Glycol/Diazolidinyl Urea/ Methylparaben/Propylparaben | 1.00 |
| Retinyl Palmitate | 0.10 |
| Butylene Glycol and Sea Whip Extract | 1.00 |
| Water, Butylene Glycol, Soy Bean (Glycine Soja) Protein | 5.00 |
| Lady's Thistle (Silybum Marianum) Extract | 0.15 |
| Ethoxydiglycol | 0.30 |
| Alpha Tocopherol | 3.00 |
| Deionized Water | Balance to 100% |

Example 2

In a second preferred embodiment of the invention, the composition of the present invention is prepared from the following components:

| Component (CTFA Name) | % by Weight |
| --- | --- |
| Glycerin | 5.00 |
| Ethoxydiglycol | 2.00 |
| Cyclopentasiloxane | 5.00 |
| Dimethicone | 2.00 |
| Dimethiconol | 0.25 |
| Cyclopentasiloxane (and) Dimethicone/Vinyl Dimethicone Crosspolymer | 0.50 |
| Dimethicone Copolyol | 0.50 |
| Grape Seed Oil | 0.50 |
| Sunflower Seed Oil | 0.50 |
| Sesame (Sesamum Indicum) Oil | 0.50 |
| Soybean Oil | 0.50 |
| Steareth 21 | 0.75 |
| Nylon-12 | 3.00 |
| Polyacrylamide (and) C13–14 Isoparaffin (and) Laureth-7 | 3.00 |
| Propylene Glycol, Water, Japanese Green Tea Extract | 0.50 |
| Biosaccharide Gum-1 | 2.00 |
| Propylene Glycol, Water, Cucumber Extract | 1.00 |
| Phenoxyethanol (and) Methylparaben (and) Butylparaben (and) Ethylparaben (and) Propylparaben | 1.00 |
| Alpha Tocopherol | 3.00 |
| Water, Butylene Glycol, Soy Bean (Glycine Soja) protein | 5.00 |
| Silybum Extract (and) Alcohol | 3.00 |
| Ylang Ylang Oil, Geranium Oil, Rose Oil, Rose Absolute, Chamomile Oil | 0.20 |
| Deionized Water | Balance to 100% |

What is claimed is:

1. A composition for application on skin, hair and nails, comprising, milk thistle extract, soybean protein, and alpha tocopherol.

2. The composition of claim 1, wherein the milk thistle extract comprises silymarin.

3. The composition of claim 2, wherein the silymarin is present in the range of 0.1 to 5.0% by weight.

4. The composition of claim 2, wherein the silymarin comprises silybin at 60–70% by weight.

5. The composition of claim 2, wherein the silymarin comprises one or more bioflavinoids selected from the group consisting of silybin, silydianin, silychristine and mixtures thereof.

6. The composition of claim 1, wherein the soybean protein comprises a mixture of soy isoflavones.

7. The composition of claim 6, wherein the mixture of soy isoflavones comprises one or more isoflavones selected from the group consisting of genistein, diadzein, and glycitein.

8. The composition of claim 7, wherein the genistein is present in the range of 0.01 to 0.03% by weight.

9. The composition of claim 7, wherein the diadzein is present in the range of 0.07 to 0.15% by weight.

10. The composition of claim 1, further comprising green tea extract.

11. The composition of claim 1, wherein the alpha tocopherol is present in the range of 1 to 5% by weight.

12. The composition of claim 2, wherein the silymarin is present in the range of 0.105 to 2.1% by weight.

13. The composition of claim 1, wherein the alpha tocopherol is present more preferably in the range of 2 to 4% by weight.

14. The composition of claim 1, wherein the alpha tocopherol is present at a concentration of 3% by weight.

* * * * *

UNITED STATES PATENT AND TRADEMARK OFFICE
CERTIFICATE OF CORRECTION

PATENT NO.    : 6,524,599 B2
DATED         : February 25, 2003
INVENTOR(S)   : Sheldon R. Pinnell It is certified that error appears in the above-identified patent and that said Letters Patent is hereby corrected as shown below:

<u>Column 4,</u>
Line 51, replace "LLTRAPURE" with -- ULTRAPURE --

<u>Column 8,</u>
Line 31, replace "is present more preferably in the range" with -- is present in the range --

Signed and Sealed this

Twenty-second Day of April, 2003

JAMES E. ROGAN
*Director of the United States Patent and Trademark Office*